(12) United States Patent
Foster (10) Patent No.: US 7,841,763 B2
(45) Date of Patent: Nov. 30, 2010

(54) BONE CEMENT MIXER WITH A DISCHARGE VALVE ATTACHED TO THE SUPPORT BASE

(75) Inventor: David Foster, Woodstock (GB)

(73) Assignee: Summit Medical Limited, Gloucestershire (GB)

( * ) Notice: Subject to any disclaimer, the term of this patent is extended or adjusted under 35 U.S.C. 154(b) by 354 days.

(21) Appl. No.: 10/592,248

(22) PCT Filed: Mar. 8, 2005

(86) PCT No.: PCT/EP2005/002446

§ 371 (c)(1),
(2), (4) Date: Jun. 7, 2007

(87) PCT Pub. No.: WO2005/084591

PCT Pub. Date: Sep. 15, 2005

(65) Prior Publication Data

US 2007/0297271 A1    Dec. 27, 2007

(30) Foreign Application Priority Data

Mar. 8, 2004  (GB) ................................. 0405203.1

(51) Int. Cl.
    *B01F 13/06* (2006.01)
(52) U.S. Cl. .................. 366/139; 366/192; 366/242
(58) Field of Classification Search ................. 366/139, 366/189, 242–252, 288, 142, 255–256, 333, 366/267; 248/94
See application file for complete search history.

(56) References Cited

U.S. PATENT DOCUMENTS

| 4,251,473 | A |   | 2/1981  | Gilbey              |
|-----------|---|---|---------|---------------------|
| 5,284,389 | A | * | 2/1994  | Lumsden ..... 366/256 |
| 5,951,160 | A | * | 9/1999  | Ronk ......... 366/130 |
| 6,974,247 | B2 | * | 12/2005 | Frei et al. ... 366/255 |
| 7,160,020 | B2 | * | 1/2007  | Sand ......... 366/139 |
| 7,168,847 | B2 | * | 1/2007  | Frei et al. ... 366/255 |
| 2002/0156483 | A1 |   | 10/2002 | Voellmicke et al. |
| 2005/0105385 | A1 | * | 5/2005  | McGill et al. ... 366/139 |
| 2006/0087912 | A1 | * | 4/2006  | Tague et al. ... 366/139 |
| 2006/0256646 | A1 | * | 11/2006 | Bidoia ......... 366/139 |
| 2007/0297271 | A1 | * | 12/2007 | Foster ........... 366/42 |

FOREIGN PATENT DOCUMENTS

| SU | 1181700 A2 |   | 6/1983  |
|----|------------|---|---------|
| SU | 1519765 A1 |   | 1/1988  |
| WO | 99/67015   | * | 12/1999 |

OTHER PUBLICATIONS

GB PTO Search Report dtd. Jun. 20, 2005.

* cited by examiner

*Primary Examiner*—Charles E Cooley
(74) *Attorney, Agent, or Firm*—Alix, Yale & Ristas, LLP (57) ABSTRACT

The invention relates to a relatively simple, low cost and effective apparatus for mixing and discharging bone cement into a discharging device such as a syringe, while also providing an improved mixing action and producing minimal fumes. The syringe may be connected to an exit port located between the first and second end of the apparatus. The apparatus is able to both prevent and enable communication between a mixing region of the apparatus and the exit port due to presence of a valve and may further comprise a base which may be integral with the valve so that movement of the base creates movement of the valve within the apparatus.

4 Claims, 7 Drawing Sheets

BONE CEMENT MIXER WITH A DISCHARGE VALVE ATTACHED TO THE SUPPORT BASE

FIELD OF THE INVENTION

The invention relates to an apparatus for mixing bone cement and discharging the mixed bone cement from a mixing container into a discharging device such as a syringe or syringes.

BACKGROUND OF THE INVENTION

Orthopedic bone cement is used in many surgical procedures throughout the world to secure hip, knee and other metallic prostheses in an appropriate anatomical position. Orthopedic bone cement is also used in procedures such as vertebroplasty, which is used to treat osteoporosis, a condition which causes progressive bone loss, creating structural weakness and skeletal fragility in hundreds of thousands of people throughout the world every year. The vertebroplasty procedure involves the injection of bone cement via a needle or syringe into a vertebral body of a patient, thereby stabilising, strengthening and reinforcing the bone and alleviating chronic back pain and preventing further vertebral damage.

Conventionally, a number of different types of bone cement may be used in a powder/liquid form; the three main types used for vertebroplasty, for example, being calcium sulphate, calcium phosphate and variations of polymethylmethacrylate (PMMA). Special formulations of PMMA have also been developed that may include, for example, the addition of barium, (e.g. for use in X-ray) and the addition of hydroxyapetite (e.g. to promote bone growth).

Since different types of bone cement are used in different procedures, and since these different types of bone cement may have different physical properties, (e.g. viscosity), the apparatus and method by which the bone cement is prepared also varies.

UK Patent No. GB 2 276 560 describes a bone cement mixing device comprising a mixing bowl with a lid having a handle extending outwardly therefrom. A mixing paddle comprising a shaft and vanes extending outwardly therefrom extends into the bowl from the lid. A step up gear mechanism is provided between the paddle and the lid such that, as the handle rotates, the paddle also rotates. The drive wheel of the gear mechanism is also caused to rotate and drives the driven wheel which causes the shaft of the paddle to rotate about its own axis as the paddle moves around the bowl.

WO 95/22402 describes a device for mixing and delivering bone cement comprising a mixing chamber, a mixing element and drive means for causing rotation of the mixing element. The drive means may be a handle axially movable relative to the mixing chamber so that a gear mechanism between the handle and the mixing element translates axial movement of the handle into rotation of the mixing element. The device may be used in conjunction with a syringe so that the cylinder of the syringe forms the body of the mixing chamber and a plunger is slidably mounted at one end of the cylinder for causing ejection of the mixed cement.

U.S. Pat. No. 5,876,116 describes an integrated bone cement mixing and discharging apparatus for use in surgical procedures for affixing prostheses to a bone or joint structure for improving the strength, rigidity and movement of the bone/joint structure. The apparatus is used for mixing the bone cement components and delivering the mixed bone cement to a desired location. The apparatus comprises a mixing chamber that is integrally combined with a delivery chamber or tube that has one end incorporating a cement delivering outlet port. The two chambers are movable between two alternate positions, a first position wherein each chamber is sealed from the other and a second position wherein the two chambers are in direct communication with each other. The mixing chamber is therefore operated independently of the delivery chamber for preparing the bone cement and once prepared, transferred from the mixing chamber through the delivery chamber or tube for immediate use.

Conventionally, for vertebroplasty, the bone cement is prepared immediately prior to each procedure by manually mixing a powder and a liquid in a bowl using a spatula or the like, and then transferring the mixed bone cement into a syringe or delivery gun for application.

One conventional method for performing vertebroplasty using a low viscosity bone cement such as PMMA involves mixing a powder and liquid in an open bowl with a spatula, then pouring, scraping or aspirating the mixture into a syringe for injection by hand into a collapsing vertebral body. In this way, the bone cement can stabilise and strengthen the bone, thereby alleviating chronic back pain and preventing further vertebral damage by reinforcing the fractured bone.

An alternative method of performing vertebroplasty comprises mixing the components in a shaker and then aspirating, via a connector, into either a 10 ml syringe or a 220 ml syringe, which is then used to fill syringes of various sizes. Following the filling of the syringes, a biopsy needle or a biopsy needle with a catheter may be connected to the syringe and the bone cement mixture injected into the vertebra of the patient.

A further method for performing vertebroplasty involves mixing the liquid and powder in a shaker or in an open bowl with a spatula (as before), aspirating or pouring the mixture into a 10 ml syringe that is used with a delivery gun, then connecting a biopsy needle or a biopsy needle with a catheter to the syringe and injecting the bone cement mixture into the vertebra of the patient.

Thus, although conventionally the mixing of bone cement may be achieved using a number of different apparatus and methods, there is no apparatus available that allows for the quick, simple and effective mixing and discharging of bone cement directly into a variety or plurality of syringes.

In general, the manual transfer of mixed bone cement from the mixing bowl or shaker to the syringes is a messy and time-consuming process. These methods also have further disadvantages in that fumes produced during the mixing of the bone cement may be a problem for operators both within the orthopedic and radiology fields.

A first aspect of the present invention provides an apparatus for mixing and discharging bone cement compounds comprising a first end and a second end, with a longitudinal axis extending between the first end and the second end, a mixing region, at least one exit port, and valve means for preventing or enabling communication between the mixing region and at least one exit port, wherein the at least one exit port is located between said first end and said second end and wherein said valve is moveable along said longitudinal axis between a first position in which the valve prevents communication between the mixing region and the at least one exit port and a second position wherein the valve enables communication between the mixing region and the at least one exit port.

Although syringes to be filled could be attached directly to the exit port(s), in a preferred embodiment, connection means are provided on the exit port(s) for the connection of syringes. These connection means may comprise valves for preventing or enabling flow through the connection means from the exit port(s) to the syringe(s). Alternatively, the exit ports may be blocked via the use of stoppers which fit into the exit ports. The connection means may be provided in different sizes or in the form of an adaptor for different sized syringes.

Since the apparatus of the present invention may be used in conjunction with a plurality of different sized adaptors, it is possible to fill a wide range of different sized syringes using the same apparatus. Additionally, since the apparatus of the present invention may comprise more than one exit port, a plurality of syringes (either the same size or different sizes) may be filled at the same time, from the same batch of mixed bone cement.

Whilst the user may be able to judge when the valve is in the open or closed position, in a preferred embodiment, the apparatus of the present invention comprises means for locating the valve in the first position and/or means for locating the valve in the second position.

In a preferred embodiment, the apparatus of the present invention also comprises means for preventing the valve from being accidentally removed from the second end of the apparatus. In one embodiment, this means comprises at least one end-stop that is provided on the exterior surface of the valve and which abuts an opposing surface, such as a ledge, that is provided on the interior surface of the apparatus.

The apparatus of the present invention may further comprise a base, which allows the apparatus to be freestanding and so increasing ease of use. Due to the fact that the exit port(s) are provided between the first and second ends, the base may be provided at the second end of the apparatus. The base may therefore act as a support on which the apparatus stands and may be integral with or attachable to the apparatus and/or the valve. The base may also be associated with the valve, so that movement of the base causes movement of the valve. In a preferred embodiment, rotation of the base causes longitudinal or axial movement of the valve. This thereby aids manipulation of the valve within the apparatus and provides a simple means for moving the valve along the longitudinal axis of the apparatus.

It is possible to provide more than one exit port between the first end and the second end, thereby allowing for the connection of a plurality of syringes so that the operator may fill more than one syringe at a time. In this way, the present invention achieves easier transfer of mixed cement to more discharging syringes or the like, with the minimum of time, mess and effort.

Thus, the present invention provides a relatively simple, low cost and effective apparatus for mixing and discharging bone cement into a syringe(s), whilst also providing an improved mixing action and producing minimal fumes.

Preferred embodiments will now be described by way of example only, with reference to the accompanying drawings.

DETAILED DESCRIPTION OF THE INVENTION

The present invention is useful with many different types of bone cement and syringe types and sizes.

Figure 1:
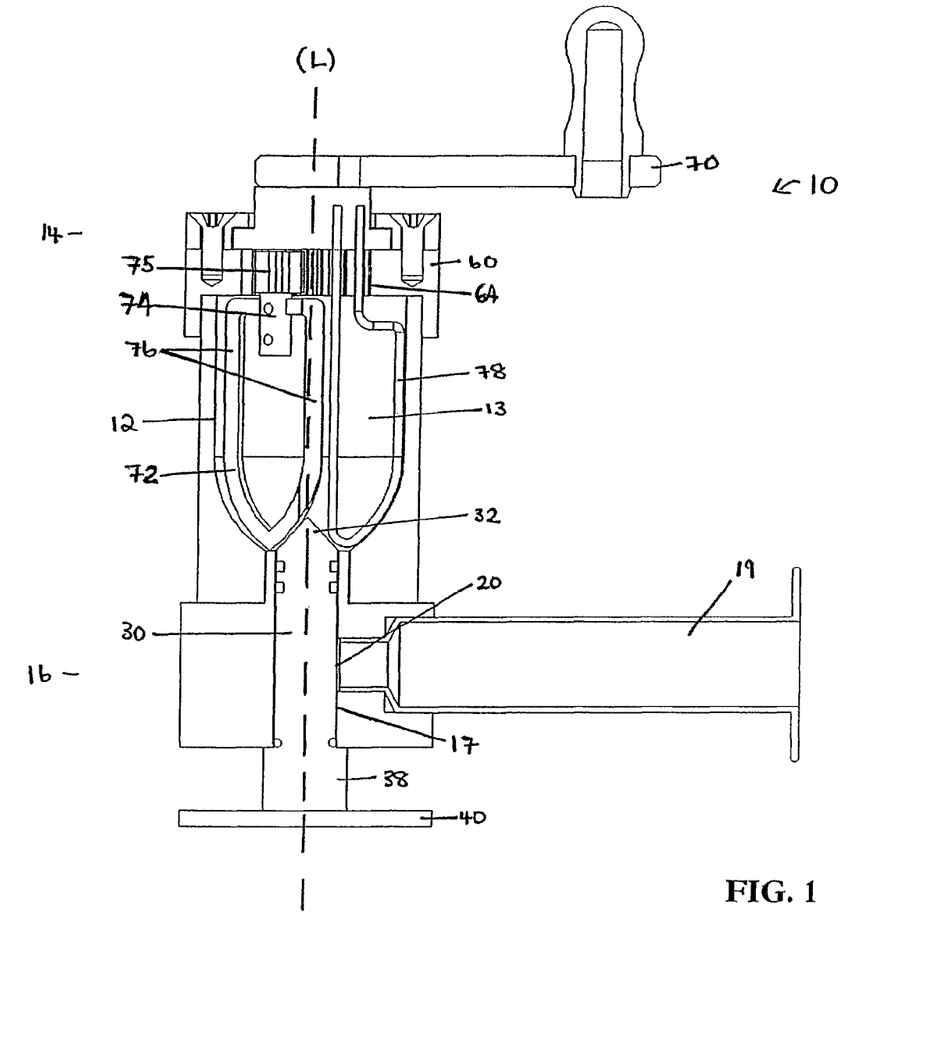
FIG. 1 is a side view of the mixing and discharging apparatus in accordance with a first embodiment of the invention, with the valve in the first position.
Figure 2:
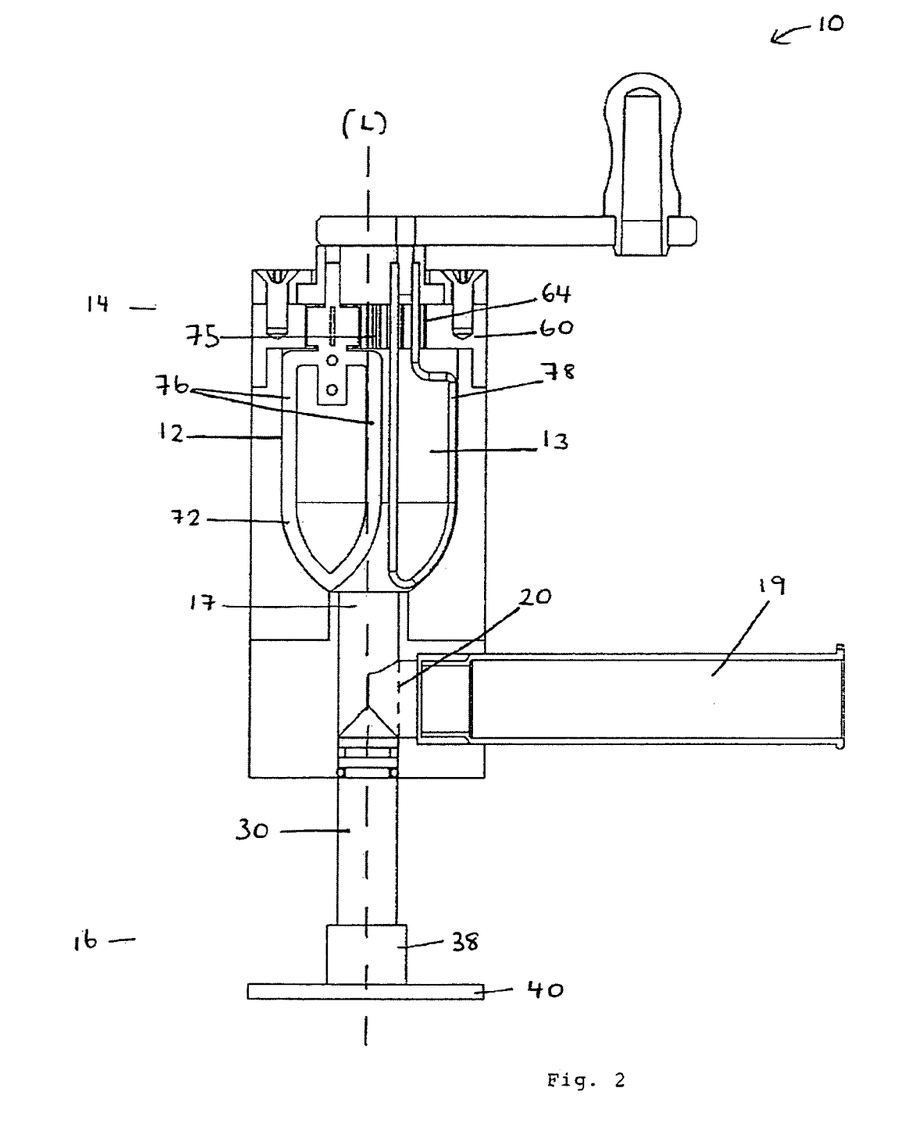
FIG. 2 is a side view of the mixing and discharging apparatus in accordance with a first embodiment of the invention, with the valve in the second position.

FIGS. 1 and 2 show one embodiment of the mixing and discharging apparatus 10. The mixing and discharging apparatus 10 comprises a first end 14, which is generally uppermost when the apparatus is in use, and a second end 16, which is lowermost when the apparatus is in use, with a longitudinal axis (L) extending between the first end 14 and second end 16. The apparatus defines a mixing and discharging container 12. In one embodiment, this comprises a bowl-shaped mixing region 13 at the first end 14, which is in communication with a cylindrical discharging region 17, at the second end 16.

During use, the operator may hold the apparatus in one hand, while mixing with the other. Alternatively, use may be simplified by standing the apparatus upright upon the flat base 40, which is provided at the second, or lowermost end 16 of apparatus. This provides added stability during mixing and discharging.

The mixing and discharging container 12 comprises at least one exit port 20 located on the side of the container between the first end 14 and the second end 16.

Figure 3:
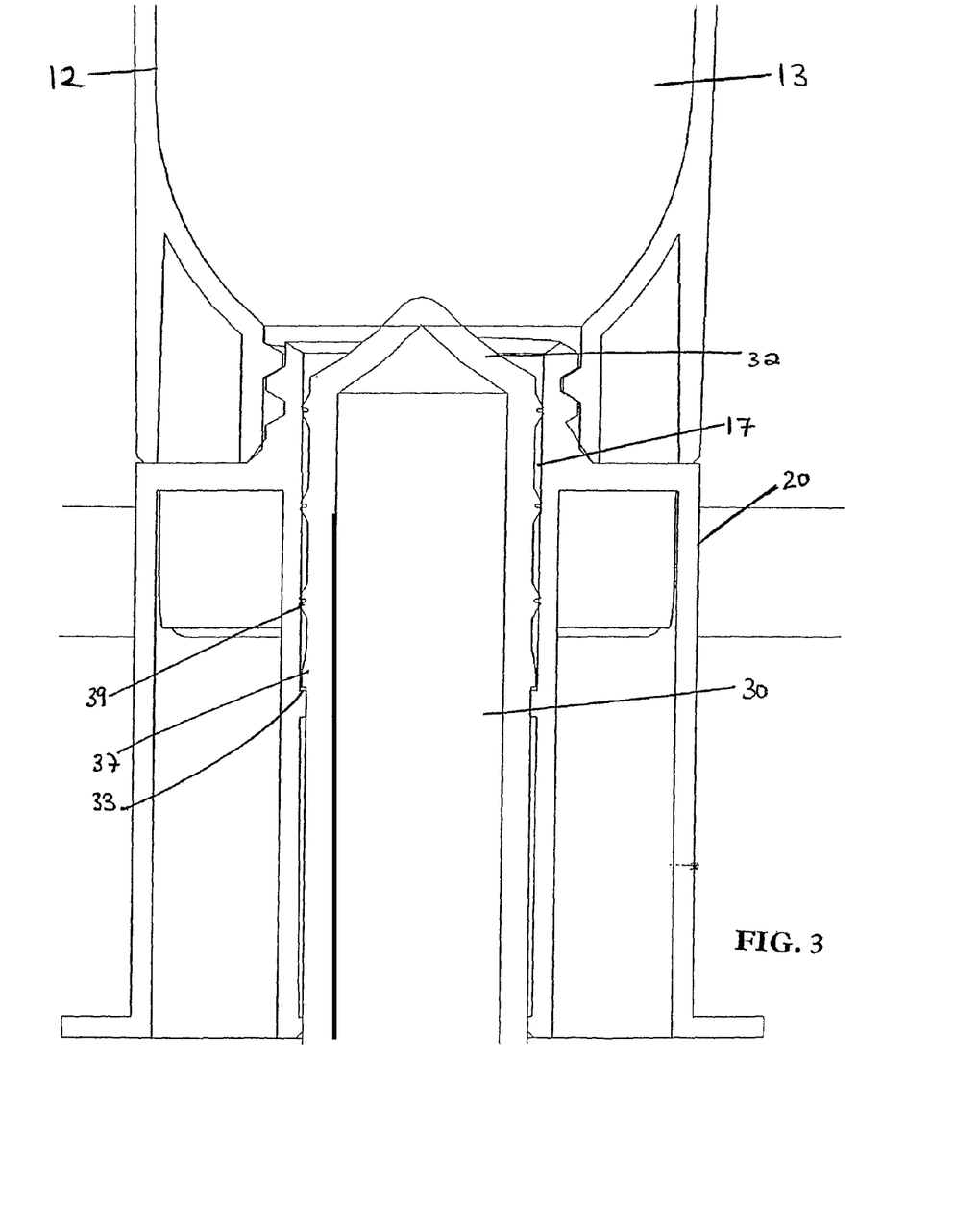
FIG. 3 is a side view of the valve positioned within the apparatus in a preferred embodiment.

The mixing and discharging apparatus 10 further comprises means for selectively preventing or enabling communication between the mixing region 13 and the exit port 20. In this embodiment, the means comprises a cylindrical valve 30, which is fitted into the discharging region 17 and is axially moveable between a first position (FIG. 1), at which the mixing region 13 and exit port 20 are prevented from being in communication with each other because the valve 30 actually blocks the exit port 20, and a second position (FIG. 2) at which the mixing region 13 and the exit port 20 are enabled to be in communication with each other, since the valve 30 no longer blocks the exit port 20. Other shapes of valve may be used, so long as the valve can be moved between an "open" (FIG. 2) and "closed" (FIG. 1) position. The exterior surface of the valve 30 may also comprise one or more moulded bi-directional friction seals 39, as shown in FIG. 3, which create a seal between the valve 30 and the interior surface of the discharging region 17 of the container 12. One end (i.e. the first, or uppermost end 32) of the valve is tapered to a point in this embodiment, to match the shape of a paddle and/or scraper, thereby minimising wastage and improving the mixing effects.

Prior to mixing, the valve of the apparatus is placed in the first position by the operator, by moving the valve along the longitudinal axis in the direction of the first end of the apparatus. Once the valve has reached the first position, an end-stop 38, provided at the second, lower end of the valve 30, abuts the second, lower end of the container, thereby locating the valve in the first position and preventing the valve from moving any further into the container. The upper end of the valve then acts as a closure for the mixing region 13, closing this region off from the discharging region 17 and the exit port(s) in the wall of the discharging region 17.

The bone cement components to be mixed are then placed in the mixing region 13 of the apparatus via an entry port (not shown), which is provided at the first end 14 of the container.

The components may then either be mixed by hand, using a spatula, or the like, or alternatively, as shown in FIGS. 1 and 2, the apparatus may further comprise a lid 60, which is adapted to fit and seal to the first end 14 of the mixing container 12. The lid may be fitted to the first end of the mixing container and locked into place in a number of ways, such as with clip means, or screw thread means.

The lid 60 may be used in conjunction with a handle 70 which is rotatably mounted in, and extending outwardly from the lid 70 and an "off-centred" paddle such as disclosed in GB 2 276 560, wherein rotation of the handle causes the paddle to rotate both around the bowl and also about its own axis. As also disclosed in GB 2 276 560, in this embodiment, the under side of the lid is preferably provided with a fixed, circular, toothed rack 64 which is coaxially arranged with the rotational axis of the handle 70. The mixing paddle 72, may comprise radially extending mixing blades 76 and be mounted on an axle 74 that is arranged coaxially with the rotational axis of the handle 70 and extends from the underside thereof. A cog wheel 75 may be fixedly attached to the upper part of the axle 74 for intermeshing engagement with the toothed rack 64. The lid 60 is preferably provided with a seal (not shown), for sealing between the lid 60 and the mixing container 12.

The present invention may further comprise a scraper paddle 78, which helps to reduce wastage, whilst also improving the mixing effect. The scraper paddle 78, shown in FIGS. 1 and 2, has a relatively thin profile to cut through cement but is shaped in the form of a paddle so as to assist in mixing, and, further, to extend out to the inner wall of the mixing region 13, to scrape cement from the interior surface of the bowl. The scraper paddle is attached to the gear mechanism such that as the handle is rotated during mixing, the scraper paddle rotates around the mixing bowl in counter-rotation with the mixing paddle shaft 74. The scraper paddle is preferably shaped so as to have a radially outer curve which essentially follows the shape of the inside surface of the mixing region 13 and a radially inner profile which is curved so as to pass by the paddle 72 during rotation.

The profile of the mixing paddle 72 in the mixing region 13 is preferably such that it will push the cement down towards the bottom of the mixing region 13, as the components are mixed. As the two components mix, the volume of cement reduces and when completely mixed, the cement will be capable of being accommodated within the cylindrical dispensing region 17.

At any time up to this point, a syringe or syringes 19 may be attached to the exit port 20, directly or, if desired, via connection means (not shown). The connection means may comprise a valve for blocking or enabling the flow of cement into the syringe.

Alternatively, simple stopper means may be connected to the exit port(s) of the apparatus for blocking exit ports to which syringes are not connected.

The connection means may also be provided in different sizes or in the form of an adaptor for different sized syringes. Due to this feature, a plurality of different sized syringes can be filled from the apparatus of the present invention, with multiple syringes being filled at the same time and from the same batch of mixed cement.

Following mixing of the bone cement and connection of the syringes or stoppers to the apparatus, the operator then moves the valve 30 into the second position (FIG. 2), by moving the valve 30 along the longitudinal axis away from the mixing region 13 of the container. End-stops 37, provided on the exterior surface of the valve eventually contact an abutment surface, e.g. a ledge 33, provided on the interior surface of the discharging region 17 of the apparatus (as shown in FIG. 3), thereby providing means for locating the valve in the second position. At this point, the valve cannot be moved any further in that direction, thereby also preventing the valve 30 from being accidentally removed from the apparatus. The valve, in this position, acts as a closure to the discharging region such that cement cannot exit the apparatus from this end.

Once the valve is in the second position and no longer blocks the exit port(s), communication is enabled between the mixing region 13 and the exit port 20 and the mixed bone cement can flow out of the mixing region 13 of the container, to the exit port 20 under the force of gravity. The operator then draws back the plunger on the attached syringe(s) 19 to remove the mixed bone cement into the syringe(s) 19, ready for use. If the cement is more viscous, the operator may also remove the lid from the apparatus and force cement down into the discharging region of the apparatus using a plunger (such as that described. hereinafter) or even a spatula. Following the filling of the syringe(s), the operator may move the valve back into the first position (FIG. 1), thereby closing the exit port(s) 20 and preventing spillage of bone cement when the syringe(s) are detached from the apparatus. This also enables a second set of syringes to be filled once the first set is detached from the apparatus.

Next, a second, preferred embodiment of the invention will be described, with reference to FIGS. 4 to 7. Corresponding features are described with like reference numerals.

Figure 4:
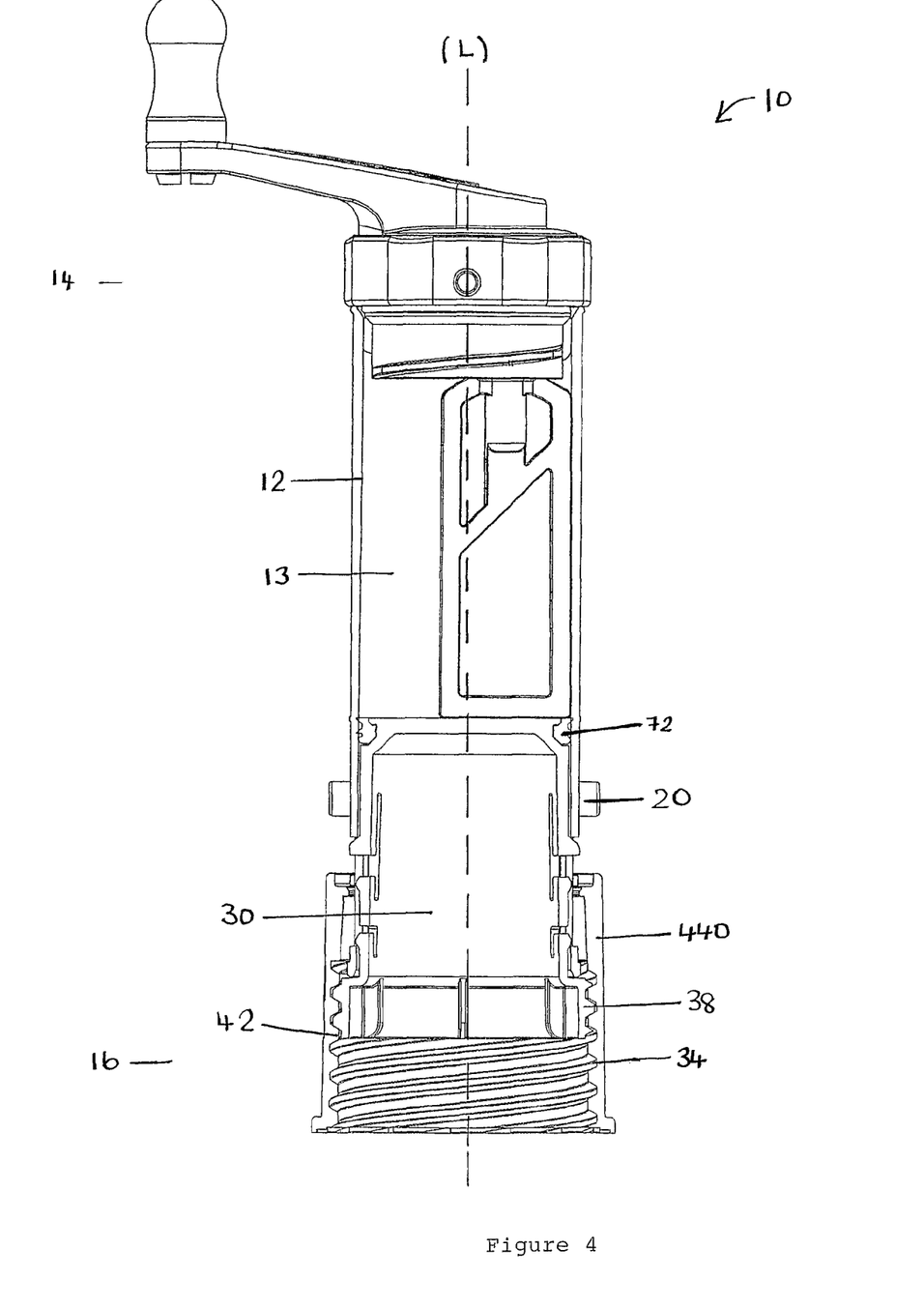
FIG. 4 is a side view of the mixing and discharging apparatus in accordance with a second embodiment of the invention.

FIG. 4 shows a second embodiment of the apparatus 10, having a first end 14 and a second end 16. The apparatus comprises a hollow, cylindrical container 12 (also shown in FIG. 5) with a mixing region 13 and an exit port or ports 20 disposed on the side of the container between the first end 14 and the second end 16.

The valve 30 is again cylindrical in shape and moveable along the longitudinal axis (L) of the apparatus between a first position (FIG. 4) wherein communication between the mixing region 13 and the exit port 20 is prevented, and a second position (FIG. 7) wherein communication is enabled.

Figure 7:
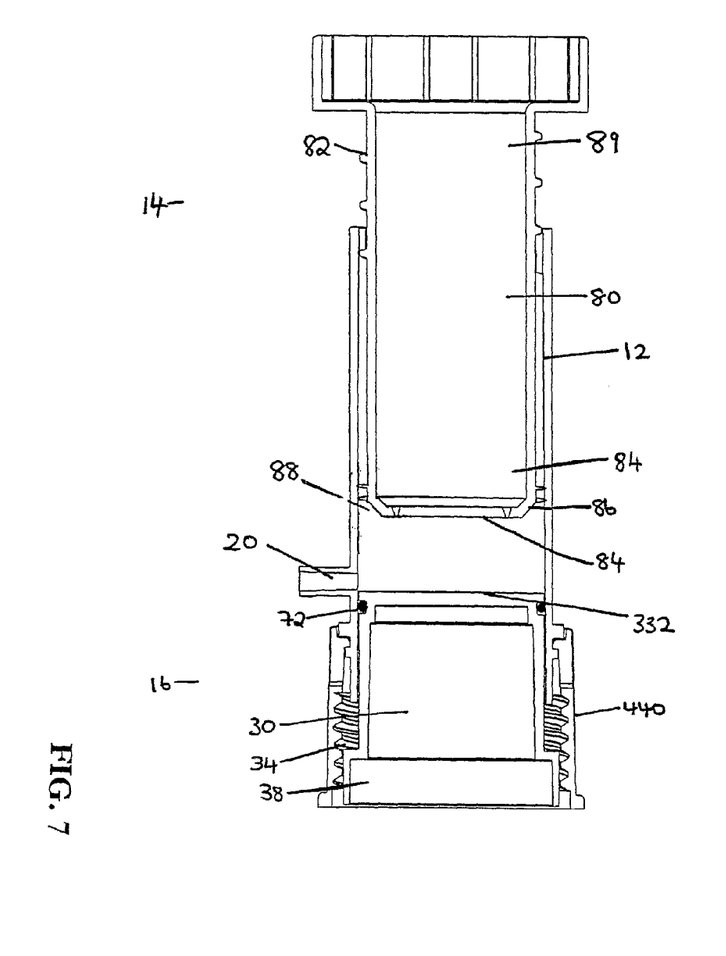
FIG. 7 is a side view of the mixing and dispensing apparatus in accordance with a second embodiment of the invention, depicting a plunger.

The exterior surface of the valve may also comprise sealing means, such as an O-ring(s) 72, as shown in FIGS. 4 and 7. The O-ring 72 provides a better seal, so that none of the components can leak from the mixing region 13 into the discharging region 17 and/or exit port(s) while it is being mixed, and also prevents air from entering the mixing region. In this way, the O-ring helps to provide a better quality cement. Alternative sealing means may also be provided on the exterior surface of the valve, and/or the interior surface of the discharging region 17 for preventing the entry of air into the mixing region 13 and for preventing unmixed or mixed bone cement or components from leaking from the mixing region 13.

As described in relation to the first embodiment, prior to mixing of the bone cement components, the valve 30 of the apparatus is placed in the first position by the operator. This may again be achieved by pushing the valve along the longitudinal axis of the container, however, in the embodiment shown in FIGS. 4 to 7, the controlled movement of the valve along the longitudinal axis is achieved via rotation of a base 440, (with which the valve is associated), relative to the container 12.

Figure 5:
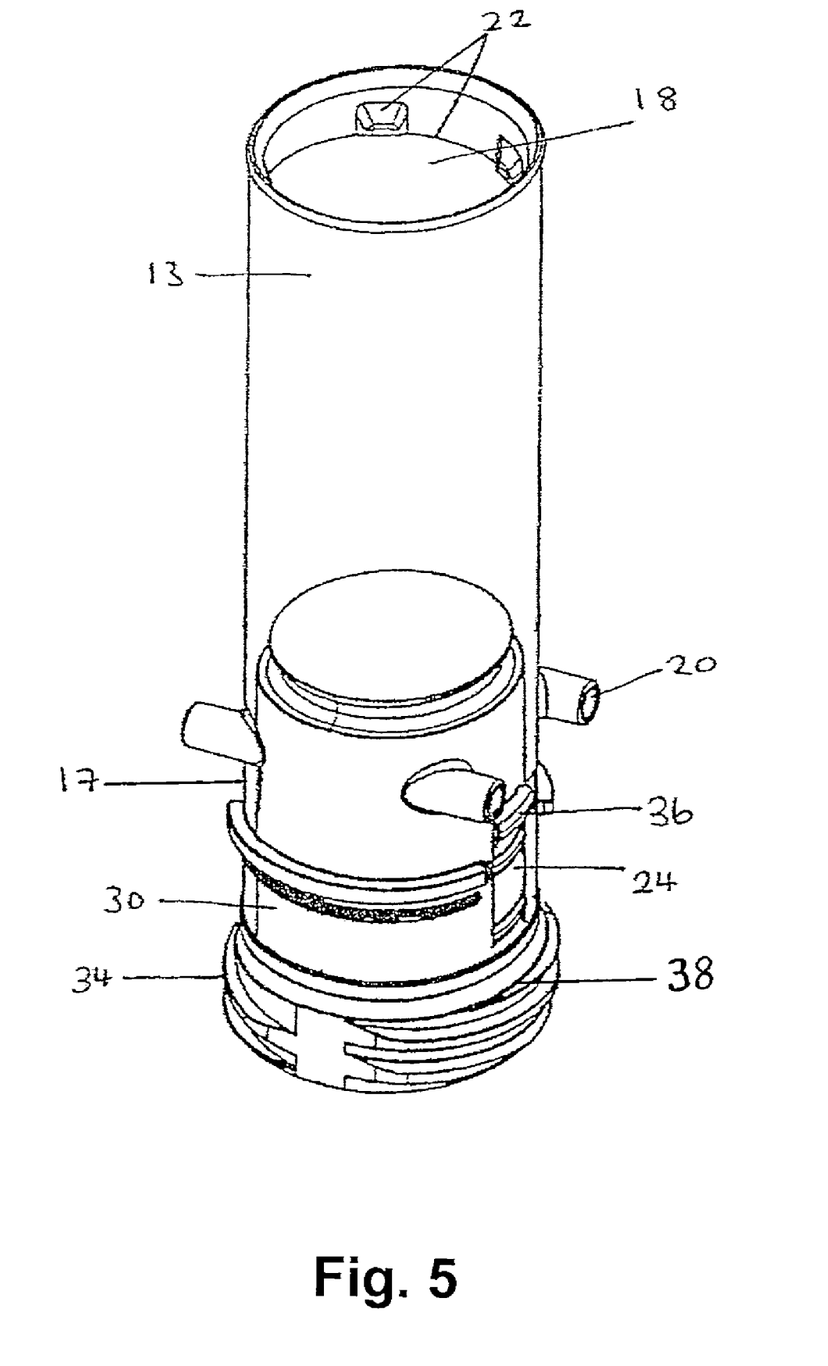
FIG. 5 is a perspective view of a preferred valve and mixing container, showing a one way clip feature.
Figure 6:
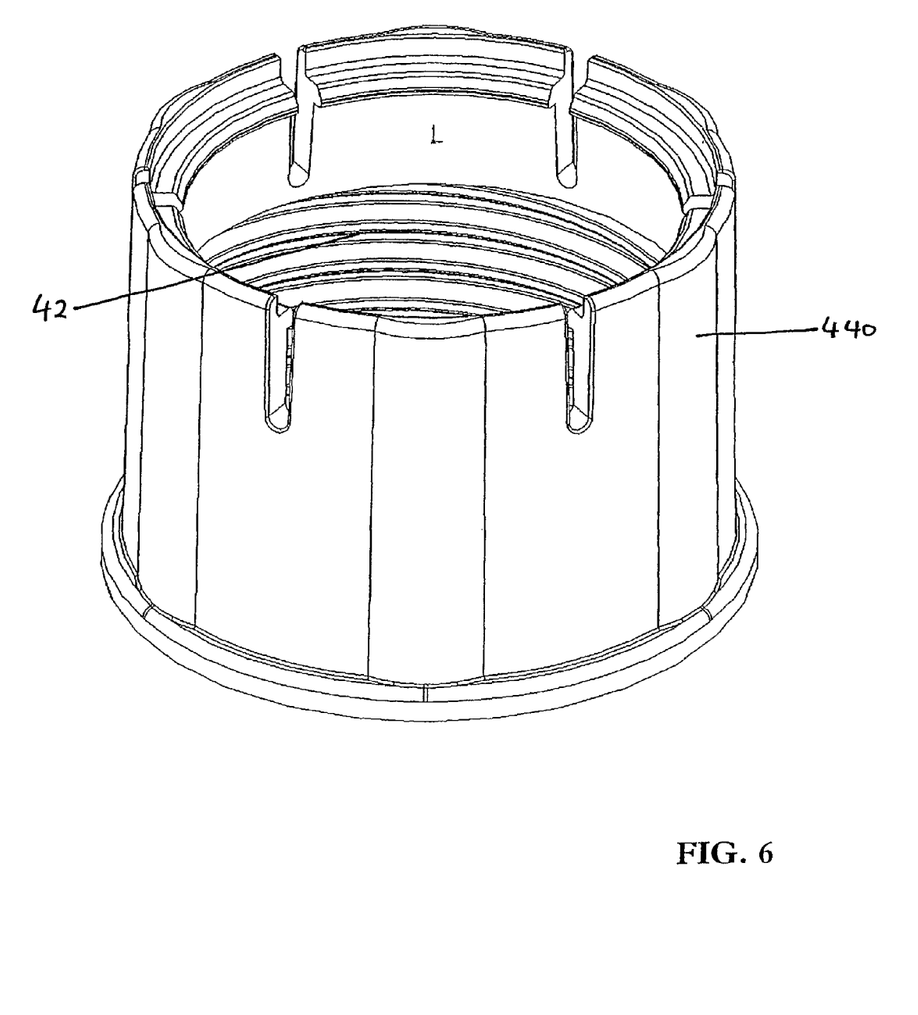
FIG. 6 is a perspective view of a preferred base.

As shown in FIG. 4, the base 440 is positioned at the second end 16 of the mixing apparatus, surrounding the second end 16 of the container 12, and a screw thread 34, formed on the exterior surface of the valve 30 or the end-stop 38 of the valve 30 (FIG. 5) is complimentary to and mates with a screw thread 42 formed on the interior surface of the base 440 (FIG. 6). Thus, rotation of the base creates movement of the valve along the longitudinal axis of the apparatus.

Means for preventing rotation of the valve 30 in relation to the mixing container 12 and means for locating the valve 30 in the first position (FIG. 4) or second position (FIG. 7), is provided in this embodiment by the way of a 'one way clip feature'. This clip feature is formed by clipping a projection 36, formed on the exterior surface of the valve 30, into an opening 24, in the side of the mixing container 12, as shown in FIG. 5. This feature limits the movement of the valve 30 along the longitudinal axis of the apparatus 10 or container 12, whilst also preventing the valve from being accidentally removed from the second end 16 of the apparatus.

After the operator has placed the valve in the first position (FIG. 4) and the mixing region is closed off from the discharging region 17 and the exit port(s) 20, the bone cement components to be mixed are then placed by the operator into the mixing container 12, via the entry port 18, which is at the first, uppermost end 14 of the apparatus.

The cement components are then mixed, either by hand, or using a lid with a handle and a paddle, as described in GB 2 276 560 and in relation to the first embodiment.

Any time up to this point, syringe(s) 19 or stopper(s) (not shown) may be attached to the exit port(s) 20, as described earlier. As also described earlier, the connection means may also be provided in different sizes or in the form of an adaptor for different sized syringes.

Once the components are fully mixed, the operator then rotates the base 440 in the opposite direction to before. The valve therefore moves along the longitudinal axis until the projection 36 of the clip abuts the end of the opening 24, preventing any further movement in that direction and thereby locating the valve in the second position (FIG. 7). At this point, communication is enabled between the mixing region 13 and the exit port(s) 20.

In some situations, such as may be the case with particularly viscous bone cement mixtures, gravity alone may not be sufficient to force the mixed bone cement from the mixing region to the vicinity of the exit port. Therefore, the apparatus may further comprise plunger means 80, as shown in FIG. 7.

Following the movement of the valve into the second position, the operator removes the lid 60 and inserts the plunger 80 into the container 12 at the first end 14, thereby forcing the mixed bone cement towards the vicinity of the exit port 20.

In order to aid insertion into the container, the plunger may comprise a screw thread 82, formed on its exterior surface, which is complimentary to, and mates with, a screw thread 22 (as shown in FIG. 5) formed on the internal surface of the mixing container 12. This is preferably the same screw thread that is used to fasten the lid in place. Therefore, by rotating the plunger 80, the plunger 80 advances into the container along the longitudinal axis.

As shown in FIG. 7, the first end 84 of the plunger which first enters the container 12 is substantially flat, with its outer perimeter 86 being cut away so that it tapers away from the end surface. Thus, when the plunger is fully inserted into the mixing and discharging apparatus, the substantially flat first end surface 84 of the plunger 80 contacts the substantially flat end surface 332 of the valve 30, and forces any remaining mixed bone cement into a small area 88 available between the tapered edge 86 of the plunger 80 and the end surface 332 of the valve 30. Due to the minimal free space available, this design thereby minimises wastage when the plunger is fully inserted into the mixing container 12.

The plunger may also comprise grooves (not shown) that extend longitudinally along its exterior surface between its first end 84 and its second end 89, so that air displaced from the mixing region due to entry of the plunger into the mixing region can escape out of the first end 14 of the apparatus. Alternatively, such grooves may be present on the interior walls of the apparatus itself. In a further arrangement, the plunger may have holes in its first 84 and second 89 end so that air between the plunger and the mixed bone cement can be vented. Due to these arrangements, air is not trapped in the apparatus with the bone cement and so is not transferred to the syringes when the cement is discharged.

Once the bone cement reaches the vicinity of the exit port, the syringe(s) can then be filled, ready for use. As described above, the valve may be moved back into the first position following the filling of the syringes, thereby ensuring that there is no spillage once the syringes are detached. This also enables a possible second filling of syringes.

The invention claimed is:

1. An apparatus for mixing and discharging bone cement compounds comprising:
    a container having a first end and a second end, with a longitudinal axis extending there between, said container defining a mixing region, and at least one exit port located between said first end and said second end,
    a valve moveable along said longitudinal axis between a first position in which the valve prevents communication between the mixing region and the at least one exit port and a second position wherein the valve enables communication between the mixing region and the at least one exit port, and
    a base, which allows the apparatus to be freestanding, and wherein the base is rotatable relative to the container but fixed axially with respect to the container and has a threaded connection with the valve, so that rotation of the base relative to the container causes axial movement of the valve from said first position to said second position.

2. The apparatus of claim 1, wherein said valve has an outside surface including a projection and said container second end includes a complementary slot, said projection engaging said slot to prevent rotation of said valve with respect to said container and guide axial movement between said first position and said second position.

3. The apparatus of claim 1, wherein said valve is coupled to said container to prevent rotation of said valve with respect to said container and to guide axial movement of said valve relative to said container.

4. The apparatus of claim 1, wherein said valve includes a projection which mates with a slot in said container, said projection engaging said slot to form a stop preventing axial movement of said valve beyond said second position.

* * * * *